United States Patent [19]
Abell et al.

[11] Patent Number: 4,571,381
[45] Date of Patent: Feb. 18, 1986

[54] HYBRID CELL LINES PRODUCING MONOCLONAL ANTIBODIES DIRECTED AGAINST NEUROTRANSMITTER DEGRADING ENZYMES

[75] Inventors: Creed W. Abell, Galveston; Richard M. Denney, Dickinson, both of Tex.

[73] Assignee: The University of Texas System Board of Regents, Austin, Tex.

[21] Appl. No.: 428,344

[22] Filed: Sep. 29, 1982

[51] Int. Cl.$^4$ .................... G01N 33/54; C12N 15/00; C12N 5/00; C12R 1/91
[52] U.S. Cl. ......................................... 435/7; 435/68; 435/172.2; 435/240; 435/948; 436/548; 935/104; 935/110
[58] Field of Search .................... 435/7, 68, 172, 240, 435/241, 948; 436/548; 424/85

[56] References Cited

U.S. PATENT DOCUMENTS 4,427,653  1/1984  Springer ................................ 435/68

OTHER PUBLICATIONS

McCauley et al, "Separation of Two Monoamine Oxidases from Bovine Bran", Molecular and Cellular Biochemistry, 1:73-81, (1973).
Craig et al, "Studies on Human Monoamine Oxidase", Monoamine Oxidase Basic and Clinical Frontiers, pp. 18-27, (1982).
Giller et al, "Molecular Properties of Platelet MAO in Psychiatric Patients and Controls", Biological Markers in Psychiatry and Neurology, pp. 111-121, (1982).
Denney et al, "Human Liver MAO-A and MAO-B Separated by Immunoaffinity Chromatography with MAO-B Specific Monoclonal Antibody", Science, 215, pp. 1400-1403, (3-1982).
Denney et al, "A Monoclonal Antibody Elicited to Human Platlet Monoamine Oxidase. Isolation and Specificity for Human MAO-A but not B", Molecular Pharmacology, 22(2), pp. 500-508, (1982).
Denney et al, "Isolation and Characterization of a Monoclonal Antibody which Binds Human Monoamine Oxidase B", Journal of Cell Biology, 91, (2,2), 96a, (9-1981).
Tzartos et al, "Production and Characterization of Monoclonal Antibodies for Use as Probes of Acetylcholine Receptors", Monoclonal Antibodies in Endocrine Research Ed., Fellows et al, pp. 69-85, (1981).
Venter et al, "The Development of Monoclonal Antibodies to B-Adrenergic Receptors and Their Use in Receptor Purification", Monoclonal Antibodies in Endocrine Research Ed., Fellows et al, pp. 119-134, (1981).
Powell et al, "Biochemical and Immunological Studies of the Monoamine-Oxidizing Activities of Cultured Human Cells", Biochemical Society Transactions, 5, pp. 180-182, (1977).
Kennett et al, "Hybrid Plasmacytoma Production: Fusions with Adult Spleen Cells, Monoclonal Spleen Fragments, Neonatal Spleen . . . ", Current Topics in Microbiology and Immunology, 81, pp. 77-91, (1977).
Cawthon et al, "Differences in A and B forms of Monoamine Oxidase Revealed by Limited Proteolysis and Peptide Mapping", Nature, 281, pp. 692-694, (1979).
Goldsby et al, "Production of Specific Antibody Without Specific Immunization", Current Topics in Microbiology and Immunology, 81, pp. 149-151, (1978).
Landowski et al, "Purification and Characterization of Human Platlet Monoamine Oxidase", FASEB Abstract, 1980.
Abell et al, "Studies of MAO Concentration and Activity in Schizophrenic Patients", in Proteins in the Nervous System, pp. 209-221, Ed. Liss, 1982.

*Primary Examiner*—Thomas G. Wiseman
*Assistant Examiner*—John E. Tarcza
*Attorney, Agent, or Firm*—Arnold, White & Durkee

[57] ABSTRACT

A continuous hybrid cell line which produces monoclonal antibody directed against the neurotransmitter degrading enzyme, monoamine oxidase B (MAO B), has been developed. The hybrid cell line was established by fusing MAO B primed, differentiated lymphoid cells with myeloma cells. Resulting fused cells were isolated, cloned and characterized as to antibody specificity against antigenic determinants of MAO B. Monoclonal antibody having specificity for MAO B and no cross reactivity with MAO A was selected and implemented in a radioimmunoassay technique for the selective measurement of MAO B concentration independent of its catalytic activity.

3 Claims, No Drawings

HYBRID CELL LINES PRODUCING MONOCLONAL ANTIBODIES DIRECTED AGAINST NEUROTRANSMITTER DEGRADING ENZYMES

BACKGROUND OF THE INVENTION

The present invention relates to hybrid cell lines capable of continuously producing monoclonal antibody specific for neurotransmitter degrading enzymes and to immunoassay methods using the monoclonal antibodies.

In recent years, the capability to produce monoclonal antibodies specific to immunogenic determinants of bacterial cells, viruses, tissue components and proteins has provided a new spectrum of diagnostic and immunotherapeutic agents.

The major intracellular enzyme responsible for the metabolic degradation of catecholamines in mammals is monoamine oxidase (MAO). This enzyme, which is located in the outer mitochondrial membrane and exists in two forms (A and B), plays an important role in the nervous system. It is also believed to function in regulating the level of pressor amines, such as phenylethylamine, in the circulation and in non-neuronal tissues. MAO catalyzes the oxidation of amines to their corresponding aldehydes, which are rapidly metabolized, usually by oxidation to an acid.

Because MAO contributes to determining the concentration of the monoamine neurotransmitters, the activity of this enzyme has been studied in patients with a wide variety of neurological and psychiatric disorders. The B form of the enzyme is found in most human tissues (with the exception of placenta, where MAO A is the predominant form) and its presence in blood platelets provides a convenient tissue for study of its activity in pathological states. In fact, platelet MAO B level has been found to be reduced in chronic schizophrenic patients compared to normals in many studies, a finding which has led investigators to focus on MAO as a possible biological marker in schizophrenia. Low platelet MAO activity, however, has also been reported in bipolar affective illness, alcoholism, Down's Syndrome, iron deficiency anemia, essential hypertension, migraine, and juvenile diabetes. In addition, low MAO activity has been associated with suicide, sensation seeking and more frequent psychiatric counseling.

As indicated above there are two types of MAO, A and B, each of which has distinct catalytic properties and is expressed in various proportions in different tissues.

MAO A is selectively inhibited by low concentration of the irreversible active site inhibitor clorgyline and preferentially oxidizes low concentrations of 5-hydroxytryptamine.

MAO B is selectively inhibited by low concentrations of deprenyl and pargyline and preferentially oxidizes low concentrations of phenylethylamine, and benzylamine.

Although the distinguishing catalytic activities of MAO A and B have been evaluated to some degree, there is little known of the structure and molecular properties of MAO A and B. MAO B, the most extensively studied of the two enzymes, has been characterized as having molecular weight of approximately 120,000 and consists of two subunits of indistinguishable molecular weight. One subunit has an essential molecule of covalently bound flavin adenine dinucleotide. Moreover, MAO may have carbohydrate residues added to its polypeptides and its lipid microenvironment is thought to contribute significantly to its catalytic activity.

Since the measured level of MAO activity is a reflection of several factors (primary structure, covalent modification, and microenvironment), it is important to examine independently MAO activity and MAO concentration. Such a dissection of activity and concentration, along with sequencing information, should clarify the fundamental structure and function of this enzyme and suggest how alterations in them, if they exist, could lead to abnormal MAO activity in psychiatric disorders.

Several assays of MAO catalytic activity, including the most commonly used radioenzymatic assay, have been developed, but only one method has been available heretofore to measure the concentration of MAO protein.

The assay of active MAO concentration involves the titration of enzyme activity with known amounts of $^3$H-pargyline. This inhibitor reacts specifically and irreversibly on a mole to mole ratio with the covalently bound FAD of MAO B. Knowing the specific activity of the $^3$H-pargyline used in the reaction permits determination of the nmoles of pargyline bound in the preparation, which in turn is equal to the nmoles of MAO in the sample. Since the method measures only catalytically active MAO, molecules are not measured which are physiologically inactive or which are inactivated during extraction or non-specifically by the incubation conditions used for $^3$H-pargyline binding.

An alternative method for determining MAO concentrations involves the use of an antibody which binds MAO B specifically. Heretofore, the reagent antibody has been an antiserum prepared from rabbits immunized with highly purified MAO B. Although this reagent was used in rocket immunoelectrophoresis to determine the concentration of MAO in platelet samples from patients, the antiserum has had limited application because of variability in animal response to the MAO antigen and the relatively low titers obtained. Such difficulties are commonly encountered in producing specific antisera.

Accordingly, in efforts to determine accurately the molecular concentration of MAO or other neurotransmitter degrading enzymes, there exists a need for unlimited quantities of an unvarying antibody reagent which recognizes a single antigenic determinant of the enzymes. Such antibody reagents are provided by this invention.

SUMMARY OF THE INVENTION

In accordance with the present invention, continuous monoclonal hybrid cell lines are established which elaborate and secrete highly specific and homogenous monoclonal antibody directed against a neurotransmitter degrading enzyme.

In its broadest aspect, the invention involves first immunizing an animal in vivo or antibody producing cells in vitro to neurotransmitter degrading enzymes. Neurotransmitter degrading enzymes include generally monoamine and catecholamine degrading enzymes such as monoamine oxidases, catechol O-methyltransferase and benzylamine oxidase. After immunization, the primed lymphocytes are recovered and fused with myeloma, plasmacytoma, or hybridoma cells to form somatic cell hybrids.

The cell hybrids are cultured, selected, and propagated in tissue culture or in vivo in ascites fluid. Thereafter the hybrid cell lines are capable of continuously producing monoclonal antibodies to the selected immunizing antigens.

Monoclonal antibodies derived and collected from an isolated hybrid cell line can be implemented in immunoassay techniques for the detection of a specific antigen in tissue samples.

DETAILED DESCRIPTION OF THE PREFERRED EMBODIMENT

The following discussion is in terms of the preferred embodiments of this invention, which represent the best mode known to the Applicants at the time of this application.

In accordance with this invention, monoclonal antibodies directed against the neurotransmitter degrading enzyme, MAO B, were isolated from continuous hybrid cell lines formed by the fusion of antigen-primed immune lymphocytes with myeloma cells.

Monoclonal antibodies are highly specific, being directed against a single antigen only. Furthermore, in contrast to conventional antibody preparations which typically include different antibodies directed against different sets of determinants on the same antigen, monoclonal antibodies are directed only against a single determinant on the antigen. Monoclonal antibodies are useful to improve the selectivity and specificity of diagnostic and analytical assay methods using antigen-antibody binding. A second advantage of monoclonal antibodies is that they are synthesized in pure form by the hybridoma culture, uncontaminated by other immunoglobulins. Monoclonal antibodies may be prepared from supernatants of cultured hybridoma cells or from ascites induced by intraperitoneal inoculation of hybridoma cells into mice.

The hybridoma technique described originally by Kohler and Milstein, *Eur. J. Immunol.* 6:511–519 (1976) has been widely applied to produce hybrid cell lines that secrete high levels of monoclonal antibodies against many specific antigens. In accordance with the production of this invention, MAO was partially purified from physiological tissue samples by ammonium sulfate precipitation and DEAE sepharose chromatgraphy. After partial purification the enzyme was labeled with $^3$H-pargyline (this irreversible inhibitor binds only to MAO in these preparations) to provide a convenient method for following the enzyme during subsequent purification steps. MAO was further purified by isoelectric focusing or chromatofocusing, and a preparation in which MAO represented 20 to 30% of the total protein was used to immunize a BALB/c mouse.

Alternatively normal and immune differentiated lymphocytes capable of producing antibody can be isolated from test animals and cultured in vitro to generate cells appropriate for producing lymphocyte hybridomas, for example such methods as in vitro stimulation of lymphocytes with mitogens and/or antigens as described by Robertson et al, *Microbiology* 1980 pp. 181–185 (1980) and Kettman et al, *J. Immunol. Methods* 39:203–222 (1980) or the splenic fragment culture method as described by Press et al, *Eur. J. Immunol.* 4:155–159 (1974).

The route and schedule of immunization of the host animal or cultured antibody producing cells therefrom are generally in keeping with established and conventional techniques for antibody stimulation and production. Applicants have employed mice as the test model although it is contemplated that any mammalian subject including human subjects or antibody producing cells therefrom can be manipulated according to the processes of this invention to serve as the basis for production of mammalian, including human, hybrid cell lines.

After immunization, immune lymphoid cells are fused with myeloma, plasmacytoma, or hybridoma cells (hereinafter referred to collectively as myeloma cells) to generate a hybrid cell line which can be cultivated and subcultivated indefinitely, to produce large quantities of monoclonal antibodies. For purposes of this invention, the immune lymphoid cells selected for fusion are lymphocytes and their normal differentiated progeny, taken either from lymph node tissue or spleen tissue from immunized animals. Applicants prefer to employ immune spleen cells, since they offer a more concentrated and convenient source of antibody producing cells with respect to the mouse system. The myeloma cells provide the basis for continuous propagation of the fused hybrid. Myeloma cells are tumor cells derived from plasma cells which show preference for bone marrow. Plasmacytoma cells are neoplastic cells derived from plasma cells. In particular, Applicants prefer to use lymphocyte hybridoma cells which secrete no immunoglobulin. Lymphocyte hybridoma cells are cells generated by the fusion of myeloma or plasmacytoma cells with normal differentiated lymphoid cells. Myeloma, plasmacytoma, and hybridomas can be selected to be devoid of immunoglobulin synthesis.

The particular species of animal from which the myeloma and immunized antibody producing cells are derived are not critical, in that it is possible to fuse cells of one species with another. However, it is preferred that the source of immunized antibody producing cells and myeloma be from the same species.

Generally the fusion techniques employed are according to the procedures set out by Kohler et al, *Eur. J. Immunol.* 6:11–19 (1976) and Kennett et al, *Lymphocyte Hybridomas—Current Topics In Microbiology and Immunology* 81:77–91 (1978) Springer-Verlag, New York. Fusion is generally accomplished by adding a suspension of antibody producing cells to the myeloma cells in growth medium and centrifuging in the presence of polyethylene glycol to form a pellet.

Products of the hybridization embodied by this invention were screened first for their ability to recognize any antigen in the chromatofocused preparation and then for their ability to indirectly immunoprecipitate $^3$H-pargyline labeled MAO B. The fusion produced approximately 300 clones. Thirty-four of the clones secreted antibody which bound to microtiter wells coated with the chromatofocused MAO and could be detected by a peroxidase-linked immunosorbent assay (ELISA). One clone produced an antibody, MAO-1C2, which recognized both pargyline inactivated and catalytically active MAO B and failed to crossreact with MAO A. Following subcloning, cells secreting MAO-1C2 were injected intraperitoneally into BALB/c mice to generate ascites fluids containing large amounts of MAO-1C2.

Alternatively, the hybrid cell lines can be continued to be cultured in vitro on cell culture media.

Moreover the hybrid cell lines can be stored and preserved in any of a number of conventional ways, including freezing and storage under liquid nitrogen. Frozen cell lines can be revived and cultured indefinitely with resumed synthesis and secretion of monoclonal antibody. The secreted antibody is recovered from tissue culture supernatant by conventional precipitation, ion exchange, affinity chromatography, or the like. The recovered antibody can be frozen and stored under refrigeration at −80° C. for at least one year without significant loss of activity.

The availability of large amounts (gram quantities) of the well characterized monoclonal antibody MAO-1C2 as provided by this invention makes it possible to measure MAO protein concentration in extracts of platelets from patients with neurological and psychiatric disorders for comparison with normal controls. Further in accordance with this invention, Applicants have developed a radioimmunoassay which is a highly reliable and specific method for determining concentration of MAO protein independent of its catalytic activity. By determining the amount of MAO protein and the catalytic activity of the enzyme in the sample, the molecular activity of MAO B in crude extracts of human platelets can be determined. In clinical studies of patients with schizophrenic, affective, and other psychiatric disorders, this methodology will permit assessment of abnormalities due primarily to altered molecular activity or enzyme concentration.

The following examples are offered to illustrate a particular embodiment of the invention but they are not intended to limit it.

A. Preparation of Antigens

The MAO preparation used for immunization was purified from outdated human blood platelets elaborating predominantly B type enzyme.

Platelet rich plasma (PRP) was obtained from The University of Texas Medical Branch Blood Bank immediately after the platelets became out-dated (72 hours after blood drawing). The PRP was stored in a cold-room overnight. In each MAO preparation, a batch of 25 units (65 ml/unit) was used.

Pooled PRP was centrifuged at $600 \times g$ for 3 min to remove contaminating red blood cells and lymphocytes. The supernatant was centrifuged at $2,500 \times g$ for 20 min and the platelets collected. The platelets were washed by dispersing in 0.9% saline-5 mM EDTA (saline-EDTA), pH 7.4, and then centrifuged at $2,500 \times g$ for 20 min. After two more washings with saline-EDTA solution, the washed platelets were suspended in cold distilled water to a final protein concentration of 5 mg/ml. The suspension was frozen at −20° C. overnight, thawed, and centrifuged at $35,000 \times g$ for 60 min. The pellet was suspended in 50 mM potassium phosphate buffer, pH 8.0, containing 0.1% Triton X-100 (freshly prepared). After the suspension was stirred for 60 min at 4° C., it was centrifuged at $35,000 \times g$ for 30 min. The pellet was resuspended in 50 mM potassium phosphate buffer, pH 8.0, containing 0.5% Triton X-100, stirred for 60 min at 4° C. and centrifuged at $150,000 \times g$ for 60 min. The supernatant containing solubilized MAO was dialyzed against $3 \times 6,000$ ml of 10 mM potassium phosphate buffer, pH 8.0, for 36-40 h.

Then the dialyzed-extracted MAO was fractionated on a DEAE-Sephacel (Pharmacia) column ($2.6 \times 40$ cm) which had been previously equilibrated with 10 mM potassium phosphate buffer, pH 8.0. The column was developed by stepwise elution with 10 mM and 100 mM potassium phosphate buffer, pH 8.0, and MAO was eluted with 100 mM potassium phosphate buffer, pH 8.0, containing 0.25% Triton X-100. The fractions containing high MAO activity were pooled together and the active protein was precipitated by adding solid $(NH_4)_2SO_4$ to 50% saturation. The mixture was centrifuged at $30,000 \times g$ for 60 min and the precipitate which floated on the surface was collected. The precipitate was dissolved in 50 mM potassium phosphate, pH 8.0, containing 1% octylglucoside.

To facilitate monitoring the enzyme during subsequent purification, MAO in the combined, active fractions from the DEAE column was labeled by treatment with 0.06 μM $^3$H-pargyline (New England Nuclear, sp. act., 50 Ci/mmol) for 30 min at 37° C. and then dialyzed against $3 \times 6,000$ ml of 0.025 M Tris-acetate buffer, pH 7.4, or 36-40 hrs. The final specifity activity of the MAO was 96,000 cpm/μg MAO protein. Estimates of quantities of $^3$H-pargyline labeled MAO are based on $^3$H cpm, assuming the specific activity reported above, and assuming a molecular weight of 120,000 for MAO. Labeling of the enzyme with $^3$H-pargyline under these conditions resulted in >90% inhibition of the enzyme. The $^3$H-pargyline labeled MAO was further fractionated on a Polybuffer Exchanger 74 (Pharmacia) chromatofocusing column ($0.9 \times 27$ cm) according to the instructions from Pharmacia Fine Chemicals. The pH gradient was developed by elution with 200 ml of eight times-diluted Polybuffer 74 (Pharmacia), pH 4.0, (adjusted with 1 M HCl) containing 1% octylglucoside. The 2.8 ml fractions were collected and were assayed for absorption at 280 nm, pH, and MAO activity. The fractions showing high MAO radio-activity near pH 5.3 were pooled together and the labeled protein fraction was precipitated by adding solid $(NH_4)_2SO_4$ to 80% saturation. The floating precipitate collected after centrifugation at $30,000 \times g$ for 20 min was washed once with 80% saturated solution of $(NH_4)_2SO_4$ in 50 mM potassium phosphate buffer, pH 7.4. The washed precipitate was dissolved in 50 mM potassium phosphate buffer, pH 8.0, containing 1% octylglucoside and dialyzed against 6000 ml of 10 mM potassium phosphate buffer, 7.4, for 24 h.

The chromatofocused preparations had specific radioactivity, 20,000-30,000 cpm/μg total protein, and it was estimated that MAO constituted 20-30% of the total protein. Virtually all the $^3$H in the DEAE-purified and chromatofocused MAO samples migrated as a single peak at a molecular weight of ca. 59,000, close to the molecular weight reported for the FAD-containing subunit of human MAO B.

B. Immunization of Animals

A BALB/c mouse was immunized by two intraperitoneal (i.p.) injections of 10 μg of $^3$H-pargyline labeled platelet MAO (days 1 and 7) contained in 0.1 ml of sterile PBS and emulsified in an equal volume of complete (first injection) or incomplete (second injection) Freund's adjuvant. The animal was boosted by i.p. injection of 10 μg of $^3$H-pargyline labeled MAO (chromatofocused material) in saline on days 54, 55, and 56, and the fusion performed on day 57.

C. Construction of Hybridomas

Hybridomas were produced by fusing spleen cells prepared on day 58 (one day following the last boost) to P3/X63 Ag8 myeloma cells with 40% polyethylene glycol 1,000 (Sigma Chemical Co.). P3/X63 Ag8 cells were obtained from Dr. Roger Kennett, Department of Human Genetics, University of Pennsylvania School of Medicine.

The hybridoma fusion techniques were performed according to the procedure of Kennett et al, *Lymphocyte Hybridomas—Current Topics in Microbiology and Immunology*, Vol. 81, pp. 77-91 (1978) Springer-Verlag, New York.

Spleens were removed aseptically from immunized mice and teased apart gently with forceps to prepare a single cell suspension in Dulbecco's Modified Eagle's Medium (DMEM). P3/X63 Ag8 cells were harvested in the logarithmic phase of growth and both cell types were collected by centrifugation at 270×g for 10 minutes at room temperature and washed three times with DMEM.

Approximately $10^8$ spleen cells were mixed together with cells in a 50 ml conical tube at a ratio of 10 viable spleen cells per viable P3/X63 Ag8 cell and the resultant cell suspension was collected in a pellet by centrifugation at 270×g for 10 minutes. The supernatant medium was removed and the tube containing the cell pellet was placed in a 37° C. water bath. A 0.2 ml portion of a warm (37° C.) 35% (wt/vol) solution of polyethylene glycol in DMEM was added to the cell pellet which was then gently mixed. The cell suspension was incubated at 37° C. for 3 minutes and was then collected by centrifugation at 270×g for 6 minutes.

Warm DMEM (5 ml) was gently dropped onto the cell pellet and the cells were suspended by gentle agitation. An additional 5 ml of warm DMEM was then added and the cells were collected by centrifugation. This final cell pellet was resuspended in 25-30 ml HY medium (see Kennett et al, supra at p. 78) and dispensed in 50 μl portions containing $1.9 \times 10^5$ cells each into 512 microtiter plate wells (Costar Plastics). Plates were incubated at 37° C. in 10% $CO_2$/air. Aminopterin (final concentrations 0.018 mg/ml) was added the day after fusion. Cells were fed on days 7 and 14 after fusion with HY medium lacking aminopterin.

D. Screening Hybridomas for Specific Antibodies

Cell culture supernates were screened initially for antibody capable of binding antigen in chromatofocused MAO which would coat microtiter plates and which could be detected by a peroxidase-linked immunosorbent assay (ELISA).

$^3$H-pargyline labeled MAO (chromatofocused material) was incubated for 4 hr at 37° C. in Cooke polystyrene microtiter plates (1 μg/ml MAO portein) in borate-saline buffer (per liter, 6.2 g $H_3BO_3$, 9.5 g $Na_2B_4O_7.10H_2O$, 9.0 g NaCl, pH 8.2). Conditioned media from wells containing growing clones were diluted 1/10 with PBS plus 0.05% Tween 20 (Sigma Chemical Co.) and incubated in the washed wells for 4 hr at 23° C. Bound mouse immunoglobulin was detected colorimetrically after a further 4 hr incubation of the washed wells with peroxidase-conjugated sheep antimouse IgG (heavy plus light chain, 1/1000 dilution from Cappel Laboratories, Cochranville, Ill.). The peroxidase reaction mix (150 μl/well) contained per 20 ml of citric acid buffer, pH 5; 8 mg o-phenylenediamine, Sigma Chemical Co.; and 4 μl of 30% hydrogen peroxide. Reactions were stopped after 2-4 min with 50 μl of 4 M sulfuric acid. Absorbance data was quantitated using an Automated ELISA reader, model MR 580 (Dynatech Laboratories).

Most cell culture supernatants gave a low level of peroxidase activity indistinguishable from control medium (fresh culture medium or medium conditioned by P3/X63 Ag8 cells), but 31 gave color reactions judged to be significantly above background. After expansion of the cell populations to ca. $5 \times 10^6$ cells for freezing in liquid nitrogen, 14 primary clones tested were strongly positive by ELISA assay. The titration curves, of the selected 14 primary clones differed markedly in shape from clone to clone, suggesting that the conditioned media contained diverse antibodies which apparently recognized a variety of antigenic determinants.

In order to determine whether any of the ELISA-positive antibodies could bind MAO, conditioned media was screened by indirect immunoprecipitation.

Conditioned media from each of the ELISA-positive hybridomas were diluted 1/10 with NET buffer (0.15 M NaCl, 5 mM EDTA, 50 mM Tris, 0.02% sodium azide, pH 7.4) containing 0.1% bovine serum albumin and 0.05% NP-40 (Particle Data Corporation), and mixed with 20-40 ng of $^3$H-pargyline labeled MAO contained in 50 μl of the same buffer. These samples were incubated in 96-well polystyrene microtiter plates (Cooke) at 23° C. for 1 hr in a rotary shaker (50 μl total volume per well). Rabbit antimouse IgG (heavy plus light chain; Cappel Laboratories, Cochranville, Ill.) was added (equivalent to 8 μg of specific antibody), and the incubation continued for 1 hr. Heat-killed fixed *Staphylococcus aureus* Cowan I (Pansorbin A; Calbiochem) was then added (50 μl of a 10% suspension), and the incubation continued for 15 min. The plate was then centrifuged for 10 min at 1700 rpm (5° C.) in a Cooke microplate carrier (Dynatech Laboratories, Alexandria, VA.) in a IEC refrigerated centrifuge (model PR-6000).

The resulting supernatants were then assayed for catalytically inactive $^3$H-pargyline labeled MAO by counting 50 μl samples dried onto 2.5 cm glass fiber filters (Reeve Angel) in toluene-based scintillation fluid (containing per L of toluene, 4g of PPO, and 0.05 g of dimethyl POPOP) or suspended in 2 ml PCS scintillation fluid (Amersham Corp. Arlington Heights, Ill.). Counting efficiency for $^3$H was 20% on dried filters or 25% in PCS when counted in a Packard-Tri-carb Liquid Scintillation Spectrometer.

Of twelve conditioned media tested, all left more than 70% of the $^3$H-pargyline labeled MAO in solution when *S. aureus* cells were used as secondary reagent. Furthermore, more than 68% of the label was left in solution when medium from eleven of the twelve primary clones (all but clone 1C2) and both *S. aureus* cells and rabbit anti-mouse IgG were present in the assay suggesting that at most a small proportion of the $^3$H-pargyline labeled MAO was immunoprecipitated by supernatants from these clones. However, one conditioned medium, 1C2, immunoprecipitated all but 15.6% of the label from the supernatant, when both secondary reagents were present. Pelleted bacteria from experiments involving 1C2 were washed by centrifugation. Bound radioactivity determination showed that a combination of (a) conditioned medium from primary clone 1C2, (b) rabbit antimouse IgG, and (c) *S. aureus* cells immunoprecipitated 20-fold more $^3$H-pargyline labeled MAO than any other sample. Under appropriate conditions, antibody from hybridoma 1C2 will precipitate at least 95% of $^3$H-pargyline labeled MAO B. Because of its ability to immunoprecipitate MAO in indirect immunoprecipitation assays, antibody from well 1C2 was studied further.

Hybridoma MAO-1C2 was grown continuously for 3 months (about 90 generations) without apparent loss of specific antibody secretion. In the meantime, eleven subclones were isolated, and supernatants from 6 of 6 subclones tested were found to secrete MAO-binding antibody as judged by their ability to immunoprecipitate $^3$H-pargyline labeled MAO in indirect immunoprecipitation tests. One of these subclones, termed MAO-1C2 #8, was injected ($3 \times 10^6 - 10^7$ cells) into pristane-primed mice to generate ascites fluid. Indirect immunoprecipitation assays indicated 1 ml of ascites fluid could bind the equivalent of 14.1 mg of MAO.

MAO-1C2 #8 was resubcloned after an additional 3 mo in culture, and 7 of 9 secondary subclones secreted anti-MAO antibody. Therefore, specific antibody secretion by this hybridoma appears to be reasonably genetically stable.

Since MAO-1C2 was elicited to pargyline-inhibited enzyme and detected by its ability to bind the same material, it was important to determine whether it could bind catalytically active enzyme. The antibody was first tested for its ability to inhibit MAO B activity in extracts of human liver mitochondria as assayed by benzylamine oxidation by the radiometric technique of Wurtman and Axelrod, *Biochem. Pharmacol.* 12:1439–1440 (1963). An extract of human liver mitochondria had significant activity ($5.15 \pm 0.057$), and the addition of MAO-1C2 scarcely reduced this at all ($4.93 \pm 0.034$), indicating that the antibody did not inhibit the enzyme, nor did MAO-1C2 alone immunoprecipitate enzyme activity. When MAO-1C2 and rabbit antimouse IgG were both added, a precipitate was formed which could be pelleted at low speed. Assays of the MAO activity in the supernatant and resuspended pellet of this sample showed that most of the activity was in the pellet (3.91 units in the pellet, 5.06 units in the pellet and supernatant combined). Since the activity recovered (5.06 units) was very close to the amount of activity added to the well (5.15 units), it is concluded that MAO-1C2 plus antimouse IgG precipitated the enzyme without inhibiting it. Furthermore, the addition of *S. aureus* cells to the mixture of enzyme plus MAO-1C2 plus antimouse IgG did not give any further inhibition or precipitation of enzyme activity.

Further indirect immunoprecipitation tests using catalytically active enzyme indicated that MAO-1C2 did not distinguish between catalytically active and $^3$H-pargyline labeled MAO. Moreover, indirect immunoprecipitation tests involving crude placental mitochondrial extract indicated MAO-1C2 monoclonal antibody did not recognize MAO A.

Furthermore, the monoclonal antibody MAO-1C2, derived ultimately from mice immunized with human MAO-B priming, does not bind either mouse or rat MAO A or MAO B.

A deposit of the hybrid cell line identified herein as MAO-1C2 is on deposit with the American Type Culture Collection and is assigned the number ATCC HB-8176.

The ability of MAO-1C2, coupled with secondary immunoglobulin reagents, to immunoprecipitate MAO B without inhibiting the enzyme or altering its substrate or inhibitor specificity makes MAO-1C2 monoclonal antibody an ideal candidate as a sensitive test component for the detection of low levels of human MAO B.

E. Immunoassay using MAO-1C2 antibody for detection of MAO B in tissue samples

All dilutions used RIA buffer (0.05 M TRIS buffer, pH 7.5, 0.14 M NaCl, $10^{-3}$ M EDTA, 0.05% NP-40, 0.1% bovine serum albumin and 0.75% octylglucoside). Incubations were done in 96-well Cooke polystyrene microtiter plates at room temperature. Samples to be tested for competition were diluted to 100 µl with RIA buffer, and mixed with $^3$H-pargyline labeled, DEAE-purified platelet MAO (DEAE 7; 25 µl, containing 3.6 µg total protein and 30 ng of MAO, as measured by $^3$H-pargyline-binding capacity). A 1/2000 dilution of ammonium sulfate-precipitated MAO-1C2 (25 µl) was added, and the microtiter plates were sealed with tape and incubated overnight with gentle rotary shaking. Rabbit antimouse (IgG 10 µl, containing 40 µg of specific antibody) was added, and the incubation continued for 1 hr. Heat-killed fixed *Staphylococcus aureus* cells (50 µl of a 10% suspension, w/v; 24) were added, and after a further incubation for 15 min, the plates were centrifuged for 15 min at $1700 \times g$ in an IEC centrifuge (model PR-6) equipped with Dynatech microplate carriers. Samples of the clear supernatant (50 to 150 µl) were removed from each well, mixed with water-miscible scintillation fluid and counted in a Packard TriCarb liquid scintillation spectrometer (counting efficiency, 54%). *Calculation of RIA Data.* Data was calculated with an Apple II Plus microcomputer equipped with Visicalc (Personal Software, Inc., Sunnyvale, Calif.), programmed to calculate the % cpm remaining in the supernatant and convert it to LN{(percent unbound)/(100-percent unbound)} (logit function). The logit function (dependent variable) for competition in the range of 25–70% was roughly linear when plotted versus log µg of protein added or log units of MAO B added. Estimates of MAO B protein concentration were calculated by linear interpolation on a standard curve relating logit value to log µg MAO in DEAE-purified platelet MAO. The total concentration of MAO B protein in the standard fraction was assumed to be equal to the concentration measured by $^3$H-pargyline binding (catalytically active enzyme).

Samples of extracts of gray matter, medulla, liver, and kidney containing 3–4 units of phenylethylamine (PEA)-oxidizing activity and of lung extract containing 0.44 units of MAO B activity were subjected to indirect immunoprecipitation radioimmunoassay using MAO-1C2, and the precipitated and unprecipitated PEA-oxidizing activities were determined.

The results indicated that in all cases except lung, >90% of the PEA-oxidizing activity was found in the immunoprecipitates, unless MAO-1C2 was omitted. Slightly less PEA-oxidizing activity (70%) was precipitated from the lung extract.

TABLE I

Specific concentration of MAO B in various tissues as measured by pargyline binding and radioimmunoassay.

| Tissue | Specific activity | Specific concentration (µg MAO/mg) | |
|---|---|---|---|
| | | Pargyline binding | RIA |
| Liver | 225 | 12.4 | 10.9 ± 1.3 |
| Lung | 16.7 | 1.14 | 1.3 ± 0.0 |
| Gray matter | 34.2 | 1.38 | 2.8 ± 0.6 |
| Medulla | 62.2 | 1.91 | 2.1 ± 0.5 |
| Kidney | 205 | 9.2 | 12.2 ± 3.5 |

The data in Table I demonstrates that in all tissues except gray matter, there was excellent agreement between values of MAO protein concentration as measured by $^3$H-pargyline binding assays (which measure only catalytically active protein) and concentration measured by the competitive assay (hereafter termed the radioimmunoassay). The radioimmunoassay appeared to detect about twice as much MAO protein in the gray matter extract as the $^3$H-pargyline binding assay. It is possible that the gray matter extract studied here had higher levels of catalytically inactive but immunologically cross-reactive MAO molecules than the other extracts.

The results presented here, which are based on a study of the interaction of MAO-1C2 with MAO B in various tissues from a single individual, suggest that MAO-1C2 may recognize human MAO B wherever it occurs.

In another series of experiments using tissues from yet another individual, it was found that MAO activity in extracts of mitochondria of kidney and brain was immunoprecipitable with MAO-1C2 as expected. Immunoprecipitable MAO B activity has also been detected in diploid human skin fibroblasts, HeLa cells, and some clones of mouse-human hybrid cells generated by the fusion of a diploid human skin fibroblast with the mouse hepatoma cell line BWTG-3. Furthermore, quantitation by competitive radioimmunoassay of MAO B in individual platelet extracts from over 60 individuals (including both psychiatric and normal subjects) that the MAO-1C2-defined determinant is associated with platelet MAO B in all samples tested. Therefore, with the data now available, it appears likely that the MAO-1C2-defined determinant is expressed on all MAO B molecules in most tissues and all human subjects.

The foregoing description of the invention has been directed to particular embodiments for purposes of explanation and illustration. It will be apparent, however, to those skilled in the art that many modifications and changes in the processes of preparing and implementing the described embodiments may be made without departing from the essence of the invention. It is applicants' intention in the following claims to cover all equivalent modifications and variations as fall within the scope of the invention as defined by the following claims.

What is claimed is:

1. A continuous monoclonal hybrid cell line which is clone MAO-1C2 identified as ATCC deposit HB-8176, developed as a fusion between a myeloma cell and a lymphocyte primed to human platelet monoamine oxidase B purified to at least 20% by weight of total protein, which hybrid cell line is capable of producing antibody which reacts with human monoamine oxidase B enzyme and does not react with human monoamine oxidase A enzyme.

2. A composition of matter consisting essentially of monoclonal antibody to human monoamine oxidase B enzyme produced by hybridoma clone MAO-1C2 of claim 1 identified as ATCC deposit HB-8176.

3. An immunoassay method for the detection of monoamine oxidase B in a tissue sample, which method comprises exposing a tissue sample extract to a composition consisting essentially of monoclonal antibody to monoamine oxidase B enzyme produced from hybridoma clone ATCC deposit HB-8176 of claim 1, and subsequently determining the extent of monoamine oxidase B enzyme-antibody binding.

* * * * *